(12) United States Patent
Yahiaoui et al.

(10) Patent No.: US 7,703,456 B2
(45) Date of Patent: Apr. 27, 2010

(54) FACEMASKS CONTAINING AN ANTI-FOG / ANTI-GLARE COMPOSITION

(75) Inventors: Ali Yahiaoui, Roswell, GA (US); Roger Bradshaw Quincy, III, Cumming, GA (US); John Gavin MacDonald, Decatur, GA (US); Eric Clayton Steindorf, Roswell, GA (US); Joel Brostin, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 396 days.

(21) Appl. No.: 10/739,531

(22) Filed: Dec. 18, 2003

(65) Prior Publication Data
US 2005/0133035 A1   Jun. 23, 2005

(51) Int. Cl.
*A62B 7/10* (2006.01)
*A62B 18/08* (2006.01)
*A62B 18/00* (2006.01)
*A61F 11/00* (2006.01)

(52) U.S. Cl. ............ 128/206.19; 128/857; 128/201.24; 128/206.13

(58) Field of Classification Search .................. 128/206.12–206.19, 863, 200.24, 200.27, 128/201.25, 205.25, 857, 206.21, 206.24, 128/206.27, 207.11, 201.15, 201.17
See application file for complete search history.

(56) References Cited

U.S. PATENT DOCUMENTS

| | | | |
|---|---|---|---|
| 2,432,484 A | 12/1947 | Moulton | |
| 2,803,552 A | 8/1957 | Stedman | |
| 3,022,178 A | 2/1962 | Park et al. | |
| 3,075,228 A | 1/1963 | Elias | |
| 3,212,909 A | 10/1965 | Leigh | |
| 3,301,701 A | 1/1967 | Baker et al. | |
| 3,380,876 A | 4/1968 | Rusher | |
| 3,396,046 A | 8/1968 | Landau | |
| 3,485,658 A | 12/1969 | Iler | |
| 3,674,531 A | 7/1972 | Shephard et al. | |
| 3,819,522 A | 6/1974 | Zmoda et al. | |
| 3,888,246 A | 6/1975 | Lauer | |

(Continued)

FOREIGN PATENT DOCUMENTS

| | | |
|---|---|---|
| JP | 11240112 A | 9/1999 |
| WO | 9700275 A2 | 1/1997 |
| WO | 9700275 A3 | 1/1997 |

OTHER PUBLICATIONS

Optical Coatings Technical Discussion from Oriel Instruments, 4 pages.
Search Report and Written Opinion for PCT/US2004/018876, Dec. 9, 2004.

*Primary Examiner*—Steven O Douglas
*Assistant Examiner*—Annette F Dixon
(74) *Attorney, Agent, or Firm*—Dority & Manning, P.A.

(57) ABSTRACT

A coating composition that is incorporated into a facemask to reduce fogging and glare is provided. For example, in one embodiment, the facemask contains a shield or visor formed from a transparent substrate having at least one surface applied with the coating composition of the present invention. The present inventors have unexpectedly discovered that one or more water-soluble organic polymers, such as ethyl hydroxyethylcellulose, may be utilized as a principal component of the coating composition to reduce fogging and glare in a simple, yet effective manner.

35 Claims, 1 Drawing Sheet

U.S. PATENT DOCUMENTS

| | | | |
|---|---|---|---|
| 3,890,966 A | 6/1975 | Aspelin et al. | |
| 3,933,407 A | 1/1976 | Tu et al. | |
| 4,095,290 A | 6/1978 | O'Brien | |
| 4,173,220 A | 11/1979 | Ratz et al. | |
| 4,177,315 A | 12/1979 | Ubersax | |
| 4,264,707 A | 4/1981 | Uozumi et al. | |
| 4,273,826 A | 6/1981 | McCollister et al. | |
| 4,309,319 A | 1/1982 | Vaugn, Jr. | |
| 4,323,063 A | 4/1982 | Fishichella | |
| 4,341,563 A | 7/1982 | Kurihara et al. | |
| 4,346,131 A | 8/1982 | Yoldas | |
| 4,367,262 A | 1/1983 | Vaughn, Jr. | |
| 4,374,158 A | 2/1983 | Taniguchi et al. | |
| 4,409,285 A | 10/1983 | Swerdlow | |
| 4,419,993 A | 12/1983 | Petersen | |
| 4,436,851 A | 3/1984 | Vaughn, Jr. | |
| 4,467,073 A | 8/1984 | Creasy | |
| 4,478,909 A | 10/1984 | Taniguchi et al. | |
| 4,539,351 A | 9/1985 | O'Malley et al. | |
| 4,551,484 A | 11/1985 | Rädisch et al. | |
| 4,589,408 A | 5/1986 | Singer | |
| 4,596,745 A | 6/1986 | Chao | |
| 4,609,688 A | 9/1986 | Rädisch et al. | |
| 4,609,729 A | 9/1986 | Garner | |
| 4,635,628 A | 1/1987 | Hubbard et al. | |
| 4,643,182 A * | 2/1987 | Klein | 128/201.25 |
| 4,662,005 A | 5/1987 | Grier-Idris | |
| 4,667,348 A | 5/1987 | Sundahl | |
| 4,719,146 A | 1/1988 | Hohage et al. | |
| 4,755,425 A | 7/1988 | Huang | |
| 4,762,736 A | 8/1988 | Garvey et al. | |
| 4,765,729 A | 8/1988 | Taniguchi | |
| 4,769,306 A | 9/1988 | Oberhauser et al. | |
| 4,816,333 A | 3/1989 | Lange et al. | |
| 4,835,194 A | 5/1989 | Bright et al. | |
| 4,844,976 A | 7/1989 | Huang | |
| 4,855,180 A | 8/1989 | Kawamura | |
| 4,856,535 A * | 8/1989 | Forbes | 128/857 |
| 4,904,525 A | 2/1990 | Taniguchi et al. | |
| 4,921,760 A | 5/1990 | Tani et al. | |
| 4,938,998 A | 7/1990 | Stock | |
| 4,940,602 A | 7/1990 | Taniguchi et al. | |
| 4,944,294 A * | 7/1990 | Borek, Jr. | 128/206.19 |
| 4,969,457 A | 11/1990 | Hubbard et al. | |
| 5,018,223 A | 5/1991 | Dawson et al. | |
| 5,020,533 A | 6/1991 | Hubbard et al. | |
| 5,021,091 A | 6/1991 | Takarada et al. | |
| 5,049,414 A | 9/1991 | Kato | |
| 5,072,460 A * | 12/1991 | Weder | 2/206 |
| 5,073,404 A | 12/1991 | Huang | |
| 5,078,915 A | 1/1992 | Sata et al. | |
| D327,141 S | 6/1992 | Hubbard et al. | |
| 5,134,021 A | 7/1992 | Hosono et al. | |
| 5,150,703 A | 9/1992 | Hubbard et al. | |
| 5,165,992 A | 11/1992 | Yajima | |
| 5,180,760 A | 1/1993 | Oshibe et al. | |
| 5,181,141 A | 1/1993 | Sato et al. | |
| 5,256,484 A | 10/1993 | Sato et al. | |
| 5,270,072 A | 12/1993 | Sato et al. | |
| 5,273,828 A | 12/1993 | Sato et al. | |
| 5,292,784 A | 3/1994 | McKinney et al. | |
| 5,387,463 A | 2/1995 | Nakamura et al. | |
| 5,393,333 A | 2/1995 | Trouve | |
| 5,407,600 A | 4/1995 | Ando et al. | |
| 5,415,815 A | 5/1995 | Bruno | |
| 5,420,015 A | 5/1995 | Wuerch | |
| 5,446,925 A | 9/1995 | Baker et al. | |
| 5,456,747 A | 10/1995 | Ibbotson | |
| 5,467,765 A | 11/1995 | Maturaporn | |
| 5,476,717 A | 12/1995 | Floch | |
| 5,480,917 A | 1/1996 | Kruger et al. | |
| 5,494,743 A * | 2/1996 | Woodard et al. | 428/336 |
| 5,496,647 A | 3/1996 | Krejci et al. | |
| 5,503,897 A | 4/1996 | Nagai et al. | |
| 5,545,713 A | 8/1996 | Krejci et al. | |
| 5,561,863 A | 10/1996 | Carlson, II | |
| 5,562,997 A | 10/1996 | Krejci et al. | |
| 5,578,378 A | 11/1996 | Kruger et al. | |
| 5,585,186 A | 12/1996 | Scholz et al. | |
| 5,607,777 A | 3/1997 | Krejci et al. | |
| 5,615,767 A | 4/1997 | Eull et al. | |
| 5,620,509 A | 4/1997 | Tampio | |
| 5,630,871 A | 5/1997 | Jordan | |
| 5,656,368 A | 8/1997 | Braun et al. | |
| 5,668,193 A | 9/1997 | Gouda et al. | |
| 5,674,941 A | 10/1997 | Cho et al. | |
| 5,679,458 A | 10/1997 | Cho et al. | |
| 5,686,602 A | 11/1997 | Farooq et al. | |
| 5,699,792 A | 12/1997 | Reese et al. | |
| 5,704,349 A | 1/1998 | Hubbard et al. | |
| 5,706,804 A * | 1/1998 | Baumann et al. | 128/206.19 |
| 5,723,175 A | 3/1998 | Scholz et al. | |
| 5,724,964 A | 3/1998 | Brunson et al. | |
| 5,743,947 A | 4/1998 | Jordan | |
| 5,744,227 A | 4/1998 | Bright et al. | |
| 5,750,054 A | 5/1998 | Cinquina et al. | |
| 5,753,373 A * | 5/1998 | Scholz et al. | 428/429 |
| 5,765,556 A | 6/1998 | Brunson | |
| 5,770,306 A | 6/1998 | Suzuki et al. | |
| 5,773,126 A | 6/1998 | Noritake et al. | |
| 5,789,476 A | 8/1998 | Iryo et al. | |
| 5,804,295 A | 9/1998 | Braun et al. | |
| 5,804,612 A * | 9/1998 | Song et al. | 523/169 |
| 5,813,398 A | 9/1998 | Baird et al. | |
| 5,814,567 A | 9/1998 | Yahiaoui et al. | |
| 5,846,650 A | 12/1998 | Ko et al. | |
| 5,851,674 A | 12/1998 | Pellerite et al. | |
| 5,854,708 A | 12/1998 | Komatsu et al. | |
| 5,873,931 A | 2/1999 | Scholz et al. | |
| 5,883,026 A | 3/1999 | Reader et al. | |
| 5,919,555 A | 7/1999 | Yakuda et al. | |
| 5,925,438 A | 7/1999 | Ota et al. | |
| 5,945,175 A | 8/1999 | Yahiaoui et al. | |
| 5,952,420 A | 9/1999 | Senkus et al. | |
| 5,962,005 A | 10/1999 | Saga et al. | |
| 5,997,621 A | 12/1999 | Scholz et al. | |
| 5,998,013 A | 12/1999 | Shoshi et al. | |
| 6,026,511 A * | 2/2000 | Baumann et al. | 2/9 |
| 6,040,053 A | 3/2000 | Scholz et al. | |
| 6,055,982 A | 5/2000 | Brunson et al. | |
| 6,074,741 A | 6/2000 | Murata et al. | |
| 6,090,489 A | 7/2000 | Hayakawa et al. | |
| 6,129,980 A | 10/2000 | Tsukada et al. | |
| 6,164,785 A | 12/2000 | Maekawa | |
| 6,165,256 A | 12/2000 | Hayakawa et al. | |
| 6,166,855 A | 12/2000 | Ikeyama et al. | |
| 6,210,858 B1 | 4/2001 | Yasuda et al. | |
| 6,213,125 B1 | 4/2001 | Reese et al. | |
| 6,214,094 B1 * | 4/2001 | Rousseau et al. | 96/15 |
| 6,217,176 B1 | 4/2001 | Maekawa | |
| 6,228,416 B1 | 5/2001 | Reibert et al. | |
| 6,231,703 B1 * | 5/2001 | Nakai | 156/60 |
| 6,248,880 B1 | 6/2001 | Karlson | |
| 6,257,235 B1 | 7/2001 | Bowen | |
| 6,279,571 B1 * | 8/2001 | Meckes | 128/201.22 |
| 6,281,468 B1 | 8/2001 | Souel et al. | |
| 6,294,008 B1 | 9/2001 | Keary et al. | |
| 6,338,855 B1 | 1/2002 | Albacarys et al. | |
| 6,340,024 B1 | 1/2002 | Brookman et al. | |
| 6,383,559 B1 | 5/2002 | Nakamura et al. | |
| 6,415,451 B1 | 7/2002 | Waller | |
| 6,420,020 B1 | 7/2002 | Yamazaki et al. | |
| 6,427,693 B1 | 8/2002 | Blackstock et al. | |
| 6,455,142 B1 * | 9/2002 | Heberger et al. | 428/215 |

| | | | | | | |
|---|---|---|---|---|---|---|
| 6,531,215 B2 * | 3/2003 | Yamazaki et al. ............ 428/336 | 6,945,656 B2 * | 9/2005 | Takahashi et al. ............ 359/601 |
| 6,572,961 B1 | 6/2003 | Koyama et al. | 6,978,782 B2 * | 12/2005 | Tayebi ................... 128/206.19 |
| 6,588,022 B1 | 7/2003 | Anders et al. | 2002/0103368 A1 * | 8/2002 | Harding et al. ................ 536/96 |
| 6,609,516 B2 | 8/2003 | Hollander et al. | 2003/0203991 A1 * | 10/2003 | Schottman et al. .......... 523/334 |
| 6,664,314 B1 | 12/2003 | Hajek et al. | 2004/0089304 A1 * | 5/2004 | Barakat et al. ......... 128/206.12 |
| 6,718,981 B2 | 4/2004 | Cardarelli | 2005/0124724 A1 * | 6/2005 | Burton et al. ................ 523/122 |
| 6,746,831 B1 * | 6/2004 | Hunt .......................... 430/350 | | | |

\* cited by examiner

US 7,703,456 B2

FACEMASKS CONTAINING AN ANTI-FOG / ANTI-GLARE COMPOSITION

BACKGROUND OF THE INVENTION

The use of protective facemasks has become standard for many health care and other related activities. The primary objective of the facemasks is to filter harmful materials from the inhaled and exhaled air. However, medical facemasks may also be used to protect the wearer from liquid insults. As such, these masks may include an attached clear plastic visor to protect the eyes from liquid splashes. Alternatively, a stand-alone clear face shield may also be worn in conjunction with the filtering mask.

One continuing problem attendant with the use of face shields or protective facemasks with attached visors in both medical and industrial applications is fogging of the visor or shield. The warm, moist air exhaled by the wearer will condense on relatively cool surfaces that are in close proximity to the nose or mouth of the user. Condensate droplets will fog or cloud eye glasses, face masks and other protective shields, along with oculars for scientific equipment, such as endoscopes and microscopes. This fogging or clouding results when a high concentration of moisture vapor contained within the protective mask passes through or around the facemask and condenses on a cooler eyeglass in the proximity of the mask. Various techniques have been proposed to solve the problem of fogging, such as described in U.S. Pat. Nos. 4,635,628; 4,419,993; 3,890,966; and 3,888,246.

Nevertheless, many of these solutions fail to solve the problem of glare. Glare is an undesirable specular reflection of light from a surface upon which the light is incident. For instance, personnel working in clean rooms and medical personnel performing lengthy, complex surgical procedures often report eye strain and eye fatigue from such reflections and glare after wearing a facemask for extended periods of time. Eye fatigue from glare is particularly noticeable when using precision scientific equipment, such as microscopes and endoscopes, while wearing a facemask or other protective equipment to protect and/or shield the wearer's face. Many commercial transparent films (e.g., polyester) used to form transparent visors or shields are coated with a thin finish; however, the impact of the finish on optical properties is negligible.

Various techniques have thus been suggested to reduce both fogging and glare in facemasks. For example, U.S. Pat. No. 5,813,398 to Baird, et al. describes a facemask having a filter body with a layer of fluid impervious film disposed over an upper portion of the facemask to block air exhaled by the wearer through the filter body from fogging eyeglasses and/or an eye piece. A layer of non-woven material is preferably placed over the fluid impervious film layer to substantially reduce and/or eliminate any glare from the fluid impervious film layer. In addition, U.S. Pat. Nos. 5,585,186 to Scholz, et al.; 5,723,175 to Scholz, et al.; 5,753,373 to Scholz. et al.; 5,873,931 to Scholz, et al.; 5,997,621 to Scholz, et al.; and 6,040,053 to Scholz, et al. generally describe coating compositions that rely on a solid particles of porous inorganic metal oxide network to impart anti-reflection properties, and very specific surfactants to impart anti-fogging properties. Unfortunately, such techniques for reducing fogging and glare in facemasks are still not adequate. For example, the use of one coating ingredient for anti-reflection (e.g., porous inorganic metal oxides) and another for anti-fogging (e.g., surfactants) is overly complex and expensive. Other issues with surfactant/solid particle dispersions relate to formulation instability over time, which can negatively affect optical properties of the product.

Currently, there is a need for an improved technique for simultaneously eliminating the deleterious effects of fogging and reducing glare on facemasks.

SUMMARY OF THE INVENTION

In accordance with one embodiment of the present invention, a facemask is disclosed that comprises a substrate, such as a transparent polyester visor or shield. A coating is present on at least one surface of the substrate that comprises one or more organic polymers as a principal component. For example, in one particular embodiment, the coating may include an alkyl hydroxyalkyl cellulose ether, such as ethyl hydroxyethyl cellulose.

In accordance with another embodiment of the present invention, a method for forming a facemask that comprises a transparent substrate is disclosed. The method comprises applying an aqueous composition to at least one surface of the transparent substrate. The aqueous composition includes a mixture of water and one or more water-soluble organic polymers. The aqueous composition is dried to form a coating on the transparent substrate, wherein the water-soluble organic polymer(s) constitute a principal component of the coating.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Figure 1:
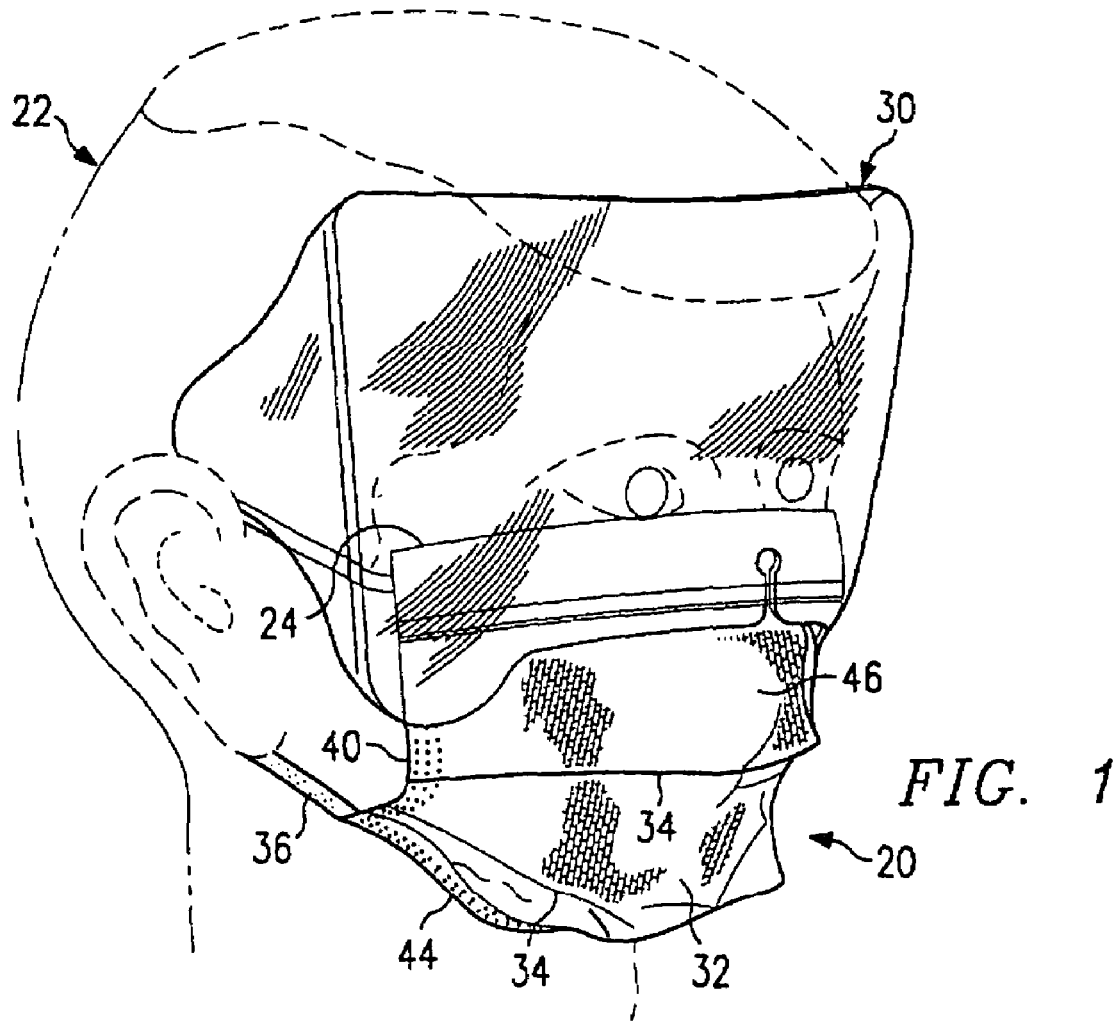
FIG. 1 is a schematic illustration of a facemask that may be formed in accordance with one embodiment of the present invention.

Repeat use of reference characters in the present specification and FIGURE is intended to represent the same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a facemask that contains a coating composition for reducing fogging and glare. For example, in one embodiment, the facemask contains a shield or visor that is utilized in conjunction with a filter body. Alternatively, the facemask may be a stand-alone shield or visor. Regardless, the shield or visor may be formed from a transparent substrate having at least one surface applied with the coating composition of the present invention. The transparent substrate to which the coating composition of the present invention is applied may be formed from a variety of different materials. Examples of such materials include, but are not limited to, polyesters, such as polyethylene terephthalate or polybutylene terephthalate; polycarbonates; allyldiglycolcarbonates; polyacrylates, such as polymethylmethacrylate; polystyrenes; polysulfones; polyethersulfone; cellulose acetate butyrate; glass; combinations thereof; and so forth. In one particular embodiment, the transparent substrate is formed from polyethylene terephthalate (PET). The transparent substrate may be in the form of a film, sheet, panel or pane of material, and may be formed by any well-known process, such as blowing, casting, extrusion, injection molding, and so forth.

The coating composition of the present invention includes one or more water-soluble organic polymers. The present inventors have unexpectedly discovered that such a water-soluble organic polymer may be utilized as the principal component of the coating composition to simultaneously reduce both fogging and glare. To minimize glare, the water-soluble organic polymer may be selected to have a nominal refractive index approximately equal to the square root of the refractive index of the transparent substrate. In some embodiments of this invention, the water-soluble organic polymer of the coating may have an average index of refraction of 1.0 to 1.7, in some embodiments from 1.2 to 1.4, and in some embodiments, from 1.25 to 1.36, which is approximately equal to the square root of the refractive indices of polyester, polycarbonate, or polymethyl methacrylate substrates. In the case of a single layer coating on a polyester film with an index of refraction of 1.7, the ideal index of refraction of the coating is 1.3, which is the square root of the ratio of the refractive index of the polyester film.

Any of a variety of water-soluble organic polymers capable of achieving the desired characteristics of transparency, reduced fogging, and reduced glare may be utilized in the present invention. For example, one class of water-soluble organic polymers found to be suitable in the present invention are polysaccharides and derivatives thereof. Polysaccharides are polymers containing repeated carbohydrate units, which may be cationic, anionic, nonionic, and/or amphoteric. In one particular embodiment, for instance, the polysaccharide is a nonionic, cationic, anionic, and/or amphoteric cellulosic ether.

Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. Nos. 6,123,996 to Larsson, et al.; 6,248,880 to Karlson; and 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the coating composition of the present invention are ethyl hydroxyethyl cellulose, methylethyl hydroxyethyl cellulose, methylethyl hydroxyethyl hydroxypropyl cellulose and methyl hydroxypropyl cellulose. In such embodiments, the hydroxyethyl groups typically constitute at least 30% of the total number of hydroxyalkyl groups, and the number of ethyl substituents typically constitutes at least 10% of the total number of alkyl substituents.

One particular example of a suitable nonionic cellulosic ether is ethyl hydroxyethyl cellulose having a degree of ethyl substitution (DS) of 0.8 to 1.3 and a molar substitution (MS) of hydroxyethyl of 1.9 to 2.9. The degree of ethyl substitution represents the average number of hydroxyl groups present on each anhydroglucose unit that have been reacted, which may vary between 0 and 3. The molar substitution represents the average number of hydroxethyl groups that have reacted with each anhydroglucose unit. Such an ethyl hydroxyethyl cellulose has a refractive index of about 1.33, which is capable of providing an anti-glare surface when coated onto a polyethylene terephthalate substrate (nominal refractive index=1.64) at a thickness of about 140 nanometers.

As stated, cationic cellulosic ethers may also be suitable for use in the present invention. Suitable cationic cellulosic ethers may include a quaternary ammonium modified cellulosic ether, such as laurdimonium hydroxethyl cellulose, steardimonium hydroxyethyl cellulose, and cocodimonium hydroxyethyl cellulose, which are commercially available from Croda Inc. of Parsipany, N.J. under the names Crodacel QL, Crodacel QS, and Crodacel QM, respectively. Other suitable cationic cellulosic ethers are described, for instance, in U.S. Pat. No. 6,338,855 to Albacarys, et al., which is incorporated herein in its entirety by reference thereto for all purposes.

Besides cellulosic ethers such as described above, various other polysaccharides may also be suitable for use in the present invention as a water-soluble organic polymer. For instance, polyglucosamines and derivatives thereof constitute another suitable class of polysaccharides that may be used in the present invention. Polyglucosamines are glucose monomer units having an amine functionality in the polysaccharide backbone. Some examples of polyglucosamines include, but are not limited to, chitin, chitosan, and polyglucosaminoglycans, which are copolymers of N-acetylglucosamine and various glycan sugars, e.g., hyaluronic acid, chondroitin, heparin, keratan and dermatan. Chitosan is a polyglucosamine obtained through deacetylation of chitin, and is more particularly a random copolymer of β-1,4-glucosamine and N-acetyl-β-1,4-glucosamine. Although normally water-insoluble, chitosan forms water-soluble salts with many organic and inorganic acids that are particularly useful in the coating composition of the present invention. Some examples of such water-soluble chitosan derivatives include, but are not limited to, acyl chitosans, carboxyalkyl chitosans, carboxyacyl chitosans, deoxyglycit-1-yl chitosans, hydroxyalkyl chitosans, or salts thereof. Particular examples include pyrrolidone carboxylic acid salt of chitosan (chitosan PCA), glycolic acid salt of chitosan (chitosan glycolate), lactic acid salt of chitosan (chitosan lactate), and monosuccinamide of chitosan (chitosan monosuccinamide or chitosanide).

The viscosity of a solution containing a water-soluble organic polymer, such as described above, may generally vary depending on the concentration of the polymer and/or other components of the solution. In most embodiments, for example, the viscosity of a solution containing a water-soluble organic polymer ranges from about 5 to about 10,000 centipoise, and in some embodiments, from about 10 to about 7,000 centipoise, as measured with a Brookfield viscosimeter, type LV, at 12 rpm and 20° C. To facilitate application of the coating composition, lower viscosities may sometimes be desired, such as from about 50 to about 1,000 centipoise, and in some embodiments, from about 150 to about 350 centipoise. The water-soluble organic polymers may sometimes be crosslinked to provide delayed hydration for handling purposes and better control of the solubilizing rate. For example, a crosslinking agent, such as glyoxal, may be used in an amount of from about 0.05 to about 2 parts by weight based on 100 parts by weight of the dry polymer.

Thus, according to the present invention, water-soluble organic polymers may be used to form a coating composition having excellent optical properties. The present inventors have unexpectedly discovered that such excellent optical properties may be achieved using water-soluble organic polymers as the principal component. That is, water-soluble organic polymers constitute at least about 50 wt. %, in some embodiments at least about 75 wt. %, and in some embodiments, at least about 90 wt. % of the coating present on the transparent substrate. In specific embodiments, for example, a nonionic cellulosic ether, such as ethyl hydroxyethyl cellulose, constitutes the principal component of the coating present on the transparent substrate. Consequently, the resulting coating may be formed in a simple, yet effective manner.

Although water-soluble organic polymers may be utilized as a principal component, other components may still be utilized the coating composition for a variety of different reasons. For instance, various of the components (e.g., surfactants) described in U.S. Pat. Nos. 5,585,186 to Scholz, et al.; 5,723,175 to Scholz, et al.; 5,753,373 to Scholz, et al.; 5,873,931 to Scholz, et al.; 5,997,621 to Scholz, et al.; and 6,040,053 to Scholz, et al., which are incorporated herein in their entirety by reference thereto for all purposes, may be used in the coating composition. When utilized, however, it is normally desired that the amounts of these components are minimized to ensure optimum compatibility and cost-effectiveness. Thus, for example, it is normally desired that surfactants (nonionic, anionic, cationic, and/or amphoteric) are contained within the coating present on the transparent substrate in an amount less than about 10 wt. %, in some embodiments less than about 5 wt. %, and in some embodiments, less than about 1 wt. % of the coating.

Various film-processing aids may also be utilized to form the coating. Examples of such film-processing aids are particles that inhibit "blocking" or sticking of the coating to itself. These particles may inhibit blocking by protruding from the surface of the coating, either individually or in the form of agglomerates. The shape and/or size of the antiblocking particles may generally vary. Typically, the antiblocking particles are contained within the coating on the transparent substrate in an amount less than about 10 wt. %, in some embodiments less than about 5 wt. %, and in some embodiments, less than about 1 wt. % of the coating. The antiblocking particles may be in the form of plates, rods, discs, bars, tubes, spheres, irregular shapes, etc. In addition, the average size (e.g., diameter) of the antiblocking particles may range from about 0.1 nanometers to about 1,000 microns, in some embodiments, from about 0.1 nanometers to about 100 microns, and in some embodiments, from about 1 nanometer to about 10 microns. For instance, "microparticles" may be utilized that have an average size of from about 1 micron to about 1,000 microns, in some embodiments from about 1 micron to about 100 microns, and in some embodiments, from about 1 micron to about 10 microns. Likewise, "nanoparticles" may also be utilized that have an average size of from about 0.1 to about 100 nanometers, in some embodiments from about 0.1 to about 50 nanometers, and in some embodiments, from about 10 to about 20 nanometers.

The antiblocking particles are generally formed from a material that does not have a substantial adverse affect on the desired optical properties of the coating. Some examples of suitable antiblocking particles include, but are not limited to, inorganic particles (e.g., silica, alumina, zirconia, magnesium oxide, titanium dioxide, iron oxide, zinc oxide, copper oxide, etc.); organic particles (e.g., polystyrene, corn starch, etc.); mineral particles (e.g., talc), and combinations thereof. For instance, alumina nanoparticles may be used in some embodiments of the present invention. Some suitable alumina nanoparticles are described in U.S. Pat. No. 5,407,600 to Ando, et al., which is incorporated herein in its entirety by reference thereto for all purposes. Further, examples of commercially available alumina nanoparticles include, for instance, Aluminasol 100, Aluminasol 200, and Aluminasol 520, which are available from Nissan Chemical Industries Ltd. Alternatively, in other embodiments, silica nanoparticles may be utilized, such as Snowtex-C, Snowtex-O, Snowtex-PS, and Snowtex-OXS, which are also available from Nissan Chemical. Snowtex-OXS particles, for instance, have a particle size of from 4 to 6 nanometers, and may be dried to a powder having a surface area of approximately 509 square meters per gram. Also, alumina-coated silica particles may be used, such as Snowtex-AK available from Nissan Chemical America of Houston, Tex. or Ludox CL particles available from Grace Davidson of Columbia, Md.

To facilitate application of the coating composition to the transparent substrate and ensure optimum transparency, the coating composition is typically formed as an aqueous solution. For example, one or more of the above-mentioned components are mixed with water to form a solution that can be applied to the transparent substrate. This solution may contain, for instance, at least about 75 wt. % water, in some embodiments at least about 90 wt. % water, and in some embodiments, at least about 96 wt. % water. The amount of the components added to the solution may vary depending on the desired thickness, the wet pick-up of the application method utilized, and/or the amount of other components utilized. For example, the amount of water-soluble organic polymers within the aqueous solution generally range from about 0.01 wt. % to about 5 wt. %, in some embodiments from about 0.1 wt. % to about 1 wt. %, and in some embodiments from about 0.2 wt. % to about 0.75 wt. %. In addition, antiblocking particles may constitute from about 0.001 wt. % to about 0.5 wt. %, in some embodiments from about 0.01 wt. % to about 0.1 wt. %, and in some embodiments from about 0.02 wt. % to about 0.08 wt. % of the aqueous solution. Other components, such as surfactants, may similarly constitute from about 0.001 wt. % to about 0.5 wt. %, in some embodiments from about 0.01 wt. % to about 0.1 wt. %, and in some embodiments from about 0.02 wt. % to about 0.08 wt. % of the aqueous solution.

The aqueous solution may be applied to the transparent substrate using any conventional technique, such as bar, roll, knife, curtain, print (e.g., rotogravure), spray, slot-die, or dip-coating techniques. When applying the coating composition to multiple surfaces, each surface may be coated sequentially or simultaneously. To ensure uniform coating and wetting of the transparent substrate, it may be oxidized prior to coating using corona discharge, ozone, plasma, or flame treatment methods. In some embodiments, the transparent substrate may also be applied with a pretreatment to facilitate uniform application of the coating composition thereto. For instance, in one embodiment, a primer is applied to the transparent substrate, such as polyvinylidene chloride (PVDC) or polyvinyl chloride (PVC). Typically, the primer does not have a substantial affect on the optical properties of the transparent substrate.

The average thickness of the resulting coating may be selected to minimize glare. Specifically, it is known that a single-layer optical coating having a thickness equal to ¼ the wavelength of incident light will result in reflections from the air-coating boundary and coating-substrate boundary that are 180° out of phase with each other, thereby causing destructive interference and reducing total reflectance. Thus, because the wavelength of visible incident light ranges from approximately 200 to 1000 nanometers, the average thickness of the coating of the present invention typically ranges from about 50 to 250 nanometers. In addition, because 550 nanometers is the wavelength at which the human eye displays a peak photo-optic response, the average coating thickness is preferably about 140 nanometers. It should be understood, however, that the coating of the present invention is not limited to a single layer, but may also contain multiple layers. For example, it is readily understood by those skilled in the art that two layers may be utilized, with each layer being optimized in refractive index and thickness to minimize reflection of different wavelengths of light, thus further enhancing the anti-glare properties over a wider spectrum of light. In addition, while the average coating thickness is desirably uniform, the actual coating thickness may vary considerably from one particular point on the coating to another. Such variations in thickness, when correlated over a visibly distinct region, may actually be beneficial by contributing to the broadband anti-reflective properties of the coating.

The coating composition of the present invention may be applied to one or both surfaces of the transparent of the substrate. When used in a facemask, the coating is generally present on at least the surface of the transparent substrate that faces the wearer. In addition, the coating may cover an entire surface of the transparent substrate, or may only cover a portion of the surface, such as a portion immediately adjacent to the eyes in a face shield. The coated substrate may be dried to remove water from the coating. For example, the coated substrate may be dried in an oven at a temperature of from about 20° C. to about 150° C., in some embodiments from about 50° C. to about 120° C., and in some embodiments, from about 100° C. to about 110° C. Once dried, the water-soluble organic polymers may constitute at least about 50 wt. %, in some embodiments at least about 75 wt. %, and in some embodiments, at least about 90 wt. % of the coating.

As stated, the coating composition reduces fogging and glare when applied to a transparent substrate in the manner set forth in the present invention. The anti-fogging property is exhibited by the tendency of the coating to resist the formation of water droplets that would otherwise significantly reduce transparency. Water vapor from, for example, human breathing, tends to condense on the coated substrate in the form of a thin uniform water film, rather than as water droplets. Such a uniform film does not significantly reduce the clarity or transparency of the substrate. Likewise, the reduction in glare is discernible through the light transmission and haze of the coated substrate. Light transmission through a coated substrate depends on the angle of incidence and the wavelength of light, and is determined using ASTM D1003 entitled "Haze and Luminous Transmittance of Transparent Plastics," which is incorporated herein by reference in its entirety for all purposes. An increase in light transmission reveals a corresponding reduction in glare. In most embodiments of the present invention, the coated substrate exhibits an increase in transmission of normal incident light of greater than about 3%, in some embodiments greater than about 5%, and in some embodiments, greater than about 8% when compared to an uncoated substrate, at a wavelength of 550 nanometers.

In addition, haze is a measurement of the wide angle scattering of light within a material. Haze may be measured with a BYK Gardner "Haze Gard Plus" instrument (BYK-Gardner USA, Columbia, Md.) using ASTM D 1003-61, procedure A, entitled "Haze and Luminous Transmittance of Transparent Plastics", which is incorporated herein by reference in its entirety for all purposes. Haze is defined as the percentage of transmitted light, which in passing through the specimen, deviates from the incident beam by more than an average of 2.5 degrees. Haze is commonly referred to as the "milkiness" of a specimen, or its loss in contrast. A negative value for the difference in haze, expressed as the difference in the percentage of haze for the coated substrate and an uncoated substrate, signifies a reduction in haze. In most embodiments of the present invention, the difference in haze is less than 0%, in some embodiments from about −1% to about −0.001%, and in some embodiments, from about −0.5% to about −0.01%.

As stated, the coated transparent substrate of the present invention is particularly useful in facemasks. In this regard, various embodiments of a facemask that may contain the coated transparent substrate will now be described in more detail. Referring to FIG. 1, for instance, one embodiment of such a facemask 20 is shown that includes a visor 30 attached to a filter body 32. The visor 30 is designed to protect the eyes and other portions of the face of a wearer 22 from liquid spray or splash. A pair of ear loops 36 (only one of which is shown in FIG. 1) is also attached to respective opposite side edges 40 of the filter body 32 for use in securing the facemask 20 over the nose and mouth of the wearer 22. If desired, surgical ties or headbands may also replace the ear loops 36.

In one embodiment, the visor 30 is formed from a transparent substrate, such as described above, and is dimensioned to fit across the width of the filter body 32 and extend over the eyes of the wearer 22. The thickness of the visor 30 may vary so that it is stiff enough to prevent collapse, yet flexible enough to bend. In some embodiments, the thickness of the visor 30 is from about 0.001 to about 1 millimeter, in some embodiments from about 0.01 to about 0.5 millimeters, and in some embodiments, from about 0.1 to about 0.2 millimeters. In one particular embodiment, the visor 30 is formed from polyethylene terephthalate (PET) and has a thickness of about 0.114 millimeters. If desired, the coating composition of the present invention may be applied to one or more surfaces of the visor 30 before and/or after it is incorporated into the facemask 20. Upon application to the visor 30, the resulting coating may inhibit air exhaled by the wearer 22 from fogging the visor 30. The coating may also minimize glare from the visor 30 that would otherwise cause eye strain or fatigue for the wearer 22. For many surgical procedures and clean room techniques, glare from a facemask may also interfere with the operation of scientific equipment having an eye piece (not shown), such as a microscope, an endoscope, or a laser sight for precision equipment.

As stated, the facemask 20 also includes a filter body 32 attached to the visor 30. The filter body 32 is designed to retard the flow of liquids to the nose and mouth of the wearer 22. The filter body 32 may be formed in any manner known to those skilled in the art. In the embodiment depicted in FIG. 1, for instance, the filter body 32 has a generally rectangular configuration defined in part by a top edge 24 opposite side edges 40 (only one of which is shown in FIG. 1), and a bottom edge 44. The filter body 32 also has multiple pleats 34 to effectively cover the nose and mouth of the wearer 22. The filter body 32 includes an exterior surface 46 and an interior surface (not shown). The pleats 34 allow the filter body 32 to bellow outwardly and easily conform to the general contours of the face of wearer 22. The pleats 34 cooperate with each other to allow the filter body 32 to expand and contract during breathing of the wearer 22, without compromising a fluid seal formed between the perimeter of the filter body 32 and adjacent portions of the face of wearer 22. With increased concern for highly toxic bacteria and chemicals, wearers of facemasks are particularly interested in preventing any fluid communication between the periphery of the facemask and adjacent portions of the wearer's face.

As will be appreciated by those skilled in the art, the filter body 32 may be constructed from any of a variety of different materials and contain any number of desired layers. In one embodiment, for instance, the filter body 32 includes four (4) distinct layers. For example, the outermost layer that defines the exterior surface 46 of the filter body 32 may be a cover stock layer that includes cellulosic fibers. The cover stock layer may be chemically coated or treated, such as with a liquid repellant, to render the cover stock resistant to liquids. A filtration layer may be positioned adjacent to the cover stock layer. The filtration layer may contain, for instance, a nonwoven web or laminate. The filtration layer inhibits the passage of airborne bacteria in either direction.

A barrier layer may be positioned adjacent to the filtration layer. One example of such a barrier material is low density polyethylene. The barrier layer may possess small pores that prevent liquids with a relatively high surface tension from passing therethrough, yet allow gases and vapors with a low surface tension to pass. The barrier layer is designed to freely pass gases in either direction, while restricting the passage of liquids in at least one direction. The porous barrier may contain compounds that absorb or react with malodorous vapors, thus imposing some restriction to vapor permeability. The cover stock and filtration layers aid the barrier layer by slowing down any liquid that may be splashed, sprayed or thrown at the filter body 32. By requiring the liquid to pass through these two outer layers prior to reaching the barrier material 34, the liquid will have less pressure and the barrier material 34 will be better able to prevent passage of the liquid. The innermost layer adjacent to the face of the wearer 22 may be constructed of a lightweight and highly porous non-woven fabric. The innermost layer is designed to prevent unwanted materials, such as facial hair, loose fibers, or beads of perspiration, from contacting the other layers, which could wick liquids through the filter body 32. The innermost layer also provides a comfortable surface for contact with the face of the wearer.

Although various configurations have been described above, it should be understood that the present invention is not limited to any particular facemask or visor configuration. For example, in one embodiment, the facemask may be formed entirely from a transparent substrate (sometimes referred to as a stand-alone "face shield") of which at least a portion is applied with the coating composition of the present invention. Various other configurations and materials used to form facemasks, including visors and filter bodies used therein, are described in U.S. Pat. Nos. 6,664,314 to Elsberg; 6,427,693 to Blackstock, et al.; 6,257,235 to Bowen; 6,213,125 to Reese, et al.; 6,055,982 to Brunson, et al.; 5,883,026 to Reader, et al.; 5,813,398 to Baird, et al.; 5,765,556 to Brunson; 5,724,964 to Brunson, et al.; 5,704,349 to Hubbard. et al.; 5,699,792 to Reese, et al.; 5,561,863 to Carlson, II; 5,150,703 to Hubbard, et al.; 5,020,533 to Hubbard, et al.; 4,969,457 to Hubbard, et al.; 4,662,005 to Grier-Idris; 4,589,408 to Singer; and D327,141 to Hubbard, et al., which are incorporated herein in their entirety by reference thereto for all purposes.

The present invention may be better understood with reference to the following examples.

Test Methods

The following test methods are utilized in the Examples.

Coating Thickness: The coating thickness was measured with an Atomic Force Microscope (AFM), which is essentially a mechanical profilometry technique having exceedingly high spatial resolution. The coated surface is very lightly scratched with a needle or other sharp, pointed surface. The scratch removes the relatively soft and friable coating without damaging the underlying surface of the hard polymer or glass substrate. The AFM is then used to profile over the edge of the scratch so that the height differential between the coating surface and the substrate surface may be measured. Alternatively, this measurement may be made from a histogram of the pixilated height data, which has the advantage of averaging out textural variations at both surfaces. A high aspect ratio tip (e.g., Park Instruments Ultralever) is used in the "contact" imaging mode. The atomic force technique is capable of measuring height variations from a maximum of 10 microns to less than 1 nanometer. Measurement points may be selected by the optical interference observed in the attached light microscope. The interference colors follow Newton's series and may be used to locate the thinnest and thickest regions of the coating to assess the full range and variability of the coating thickness in any single sample.

Fogging: Fogging was evaluated by directly breathing onto the film held approximately one inch from the mouth. Fogging was determined subjectively to be (i) "excellent" if no fogging of the film was observed; (ii) "fair" if fogging was observed but dissipated within 2 seconds; or (iii) "poor" if fogging persisted more than 2 seconds. If excellent or fair, the coating was said to have "antifogging" properties.

Glare: Glare is assessed by measuring the percent of light transmission through the substrate. The percent light transmission depends on the angle of incidence and the wavelength of light. Light transmission is measured using 500 nm light, which is about the median of the visible light range, and is determined using ASTM method D1003-92 entitled "Haze and Luminous Transmittance of Transparent Plastics", using BYK Gardner "Haze Gard Plus" instrument (BYK-Gardner USA, Columbia, Md.). Higher light transmission values correspond to less glare.

Haze: Haze is a measurement of the wide angle scattering of light within a material. Haze was measured with a BYK Gardner "Haze Gard Plus" instrument (BYK-Gardner USA, Columbia, Md.) using ASTM D 1003-61, procedure A, entitled "Haze and Luminous Transmittance of Transparent Plastics."

EXAMPLE 1

The ability to inhibit fogging and glare with a coating composition of the present invention was demonstrated. Coating compositions were formed from a variety of different water-soluble organic polymers. One such water-soluble organic polymer was Bermocoll E 230FQ, which is ethyl hydroxyethyl cellulose commercially available from Akzo Nobel of Stamford Conn. Another water-soluble organic polymer was Hydagen CMF, which is chitosan glycolate commercially available from Cognis Corporation of Ambler, Pa. Another water-soluble organic polymer was Crodacel QM, which is PG-hydroxyethyl cellulose cocodimonium, a quaternary ammonium cellulose salt available from Croda, soluble Inc. of Parsipany, N.J. Finally, the other water-soluble organic polymer was Klucel EF, which is hydroxypropyl cellulose commercially available from Hercules, Inc. of Wilmington, Del.

The active percentage of the ingredients within each coating composition (the balance in each sample being water) is set forth below in Table 1.

TABLE 1

Active Wt. % of Samples 1-23

| Composition | Bermocoll E 230FQ | Hydagen CMF | Klucel EF | Crodacel QM | Gelatin | Surfactant(s) | Solvent | Particles | Antimicrobial Agent |
|---|---|---|---|---|---|---|---|---|---|
| 1 | 0.25 | 0 | 0 | 0 | 0 | 0 | 0 | 0 | 0 |
| 2 | 0.25 | 0.025 | 0 | 0 | 0 | 0 | 0 | 0 | 0 |
| 3 | 0.25 | 0.025 | 0 | 0 | 0 | 0 | 0.50 | 0.10 | 0 |
| 4 | 0.50 | 0.050 | 0 | 0 | 0 | 0 | 0 | 0.10 | 0 |
| 5 | 1.00 | 0.100 | 0 | 0 | 0 | 0 | 0 | 0 | 0 |
| 6 | 1.00 | 0.100 | 0 | 0 | 0 | 0 | 0.50 | 0.05 | 0 |
| 7 | 0.50 | 0.100 | 0 | 0.20 | 0 | 0 | 0 | 0 | 0 |
| 8 | 0.50 | 0 | 0.50 | 0 | 0 | 0 | 0 | 0 | 0 |
| 9 | 0 | 0 | 0.50 | 0 | 0 | 0 | 0 | 0 | 0 |
| 10 | 0.50 | 0 | 0 | 0 | 0 | 0.20 | 0 | 0 | 0 |
| 11 | 0 | 0.050 | 0 | 0 | 0.03 | 0 | 0 | 0.40 | 0 |
| 12 | 0.40 | 1.800 | 0 | 0 | 0 | 0 | 0 | 0 | 0 |
| 13 | 0 | 0 | 0 | 0 | 0 | 0.46 | 0 | 0 | 0 |
| 14 | 0 | 0 | 0 | 0 | 0 | 0.90 | 0 | 0 | 0 |
| 15 | 0 | 0 | 0 | 0 | 0 | 0.43 | 0 | 0.96 | 0 |
| 16 | 0.25 | 0 | 0 | 0 | 0 | 0.47 | 0 | 0 | 0 |
| 17 | 0.25 | 0 | 0 | 0 | 0 | 0 | 0 | 0 | 1.0 |
| 18 | 0.24 | 0 | 0 | 0 | 0 | 0.71 | 0 | 0 | 0 |
| 19 | 0 | 0 | 0.48 | 0 | 0 | 0 | 0 | 0.40 | 0 |
| 20 | 0 | 0 | 0 | 0 | 0 | 0.29 | 0 | 0 | 0 |
| 21 | 1.00 | 0 | 0 | 0 | 0 | 0 | 0 | 0 | 0 |
| 22 | 0.92 | 0 | 0 | 0 | 0 | 0.06 | 0 | 0 | 0 |
| 23 | 0.90 | 0 | 0 | 0 | 0 | 0.06 | 0 | 0.05 | 0 |

Besides a water-soluble organic polymer, some of the samples also contained other ingredients. For instance, samples 10, 13-16, 18, 20, and 22-23 contained one or more surfactants. Specifically, sample 10 utilized 0.20 wt. % Glucopon 220 UP, which is an alkyl polyglycoside available from Cognis. Sample 13 utilized 0.46 wt. % sodium cocoyl glutamate (an anionic surfactant available from Hampshire Chemicals). Sample 14 utilized 0.46 wt. % sodium cocoyl glutamate (Hampshire Chemicals) and 0.44 wt. % lauryl ethylenediaminetriacetate, sodium salt (NaLED3A) (a chelating surfactant available from Hampshire Chemicals). Sample 15 utilized 0.43 wt. % sodium cocoyl glutamate (Hampshire Chemicals). Sample 16 utilized 0.47 wt. % sodium cocoyl glutamate (Hampshire Chemicals). Sample 18 utilized 0.30 wt. % triethanolamine cocoyl glutamate (an anionic surfactant available from Hampshire Chemicals) and 0.41 wt. % NaLED3A (Hampshire Chemicals). Sample 20 contained 0.29 wt. % Sugaquat S-1210, which is a $C_{12}$ polyglycoside di-substituted with a $C_{18}$ quaternary ammonium group commercially available from Colonial Chemical, Inc. of South Pittsburg, Tenn. Finally, samples 22-23 each contained 0.06 wt. % Sugaquat S-1210 (Colonial Chemical).

In addition, samples 3-4, 6, 11, 19, and 23 contained Snowtex-AK particles, which are colloidal alumina-coated silica particles commercially available from Nissan Chemical Industries, Ltd. of Houston, Tex. Likewise, sample 15 contained Nalco 2326 particles, which are colloidal silica particles commercially available from Ondeo Nalco Co. of Naperville, Ill. Further, sample 11 utilized a gelatin, i.e., type A from porcine skin, which is commercially available from Sigma-Aldrich Co. of Milwaukee, Wis. Samples 3 and 6 also included an isopropyl alcohol solvent commercially available from Sigma-Aldrich Co. Finally, sample 17 included AEM 5772, which is an antimicrobially-active material that contains an organosilane quat, i.e., 3-(trimethoxysilyl) propyloctadecyldimethyl ammonium chloride, and methanol, and is commercially available from Aegis Environments Co. of Midland, Mich.

The coating compositions were applied to a clear polyester film obtained from Dupont of Wilmington, Del. under the name "Melinex® 516." Samples were formed in which only one surface of the polyester film was applied with the coating composition and in which both surfaces of the polyester film was applied with the coating composition. To apply the coating, the ingredients of each composition were initially dispersed in deionized water. The resulting dispersion was thoroughly mixed at a temperature of less than 45° C. (or ambient temperature). The mixing was performed until a clear solution was obtained. Coating of the polyester film was performed by drawing the solution over the film with a Mayer rod. The coating thickness was controlled by the size of the grooves on the Mayer rod. A coating thickness was targeted so that the dried coated film yielded a blue/purple hue. Drying was carried out in a hot air convection oven at about 110° C. for about 1 minute. Coatings were applied sequentially, i.e., one side at a time.

Once coated, the fogging characteristics, light transmission, and difference in haze were measured for each sample. In some cases, multiple samples were tested for a single composition, with the average of the samples being reported. Multiple uncoated samples (control) were also tested for comparison. The results are set forth below in Tables 2 and 3, with Table 2 providing the results for the samples having only one side coated and Table 3 providing the results for the samples having each side coated.

TABLE 2

Properties of the Samples with One Side Coated

| Sample | Antifogging? | Avg. Light Transmission (%) | Avg. ΔHaze |
|---|---|---|---|
| 1 | Yes | 92.7 | −0.14 |
| 2 | Yes | 93.1 | 0.00 |
| 3 | Yes | 92.4 | −0.20 |
| 4 | Yes | 93.9 | −0.10 |
| 5 | Yes | 91.9 | −0.01 |
| 6 | Yes | 92.7 | −0.18 |
| 7 | Yes | 92.7 | −0.18 |
| 11 | Yes | 93.5 | +1.00 |

TABLE 2-continued

Properties of the Samples with One Side Coated

| Sample | Antifogging? | Avg. Light Transmission (%) | Avg. ΔHaze |
|---|---|---|---|
| 12 | Yes | 93.3 | +0.14 |
| 13 | Yes | 94.0 | −0.04 |
| 14 | Yes | 93.5 | +0.03 |
| 15 | Yes | 94.3 | −0.14 |
| 16 | Yes | 93.6 | −0.15 |
| 20 | Yes | 92.3 | +0.70 |
| 21 | Yes | 94.2 | −0.06 |
| 22 | Yes | 94.3 | −0.05 |
| 23 | Yes | 94.3 | +0.68 |

TABLE 3

Properties of the Samples with Two Sides Coated

| Sample | Antifogging? | Avg. Light Transmission (%) | Avg. ΔHaze |
|---|---|---|---|
| 1 | Yes | 95.5 | −0.20 |
| 2 | Yes | 96.3 | −0.15 |
| 3 | Yes | 95.2 | +0.10 |
| 4 | Yes | 98.5 | +0.13 |
| 5 | Yes | 95.1 | −0.11 |
| 6 | Yes | 95.2 | +0.13 |
| 7 | Yes | 95.7 | +1.88 |
| 8 | Yes | 93.5 | +1.07 |
| 9 | Yes | 93.7 | +0.30 |
| 10 | Yes | 96.2 | −0.15 |
| 17 | Yes | 92.6 | +0.28 |
| 18 | Yes | 95.4 | −0.12 |
| 19 | Yes | 95.6 | +0.68 |

None of the control samples were determined to have antifogging properties. In addition, the light transmission of the control samples was generally less than the light transmission of the samples formed according to the present invention. Thus, as indicated above, the coating composition of the present invention achieved reduced fogging and glare in comparison to the control samples.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A facemask comprising a substrate, wherein a coating is present on at least one surface of said substrate, the coating having a thickness of from about 50 to about 250 nanometers and consisting essentially of organic polymers, wherein the organic polymers include a cellulosic ether and constitute at least about 90 wt. % of said coating, and the substrate forms a visor or shield of the facemask.

2. A facemask as defined in claim 1, wherein said substrate is transparent.

3. A facemask as defined in claim 1, wherein said substrate is a polyester film.

4. A facemask as defined in claim 1, wherein said coating comprises at least one organic polymer having an index of refraction of from 1.0 to 1.7.

5. A facemask as defined in claim 1, wherein said coating comprises at least one organic polymer having an index of refraction of from 1.2 to 1.4.

6. A facemask as defined in claim 1, wherein said coating comprises at least one organic polymer having an index of refraction of from 1.25 to 1.36.

7. A facemask as defined in claim 1, wherein said cellulosic ether is nonionic.

8. A facemask as defined in claim 7, wherein said nonionic cellulosic ether is selected from the group consisting of alkyl cellulose ethers, hydroxyalkyl cellulose ethers, alkyl hydroxyalkyl cellulose ethers, and combinations thereof.

9. A facemask as defined in claim 8, wherein said nonionic cellulosic ether includes an alkyl hydroxyalkyl cellulose ether.

10. A facemask as defined in claim 9, wherein said nonionic cellulosic ether includes ethyl hydroxyethyl cellulose.

11. A facemask as defined in claim 1, wherein said cellulosic ether is cationic.

12. A facemask as defined in claim 11, wherein said cellulosic ether is modified with a quaternary ammonium group.

13. A facemask as defined in claim 1, wherein said coating comprises less than about 10 wt. % of surfactants.

14. A facemask as defined in claim 1, wherein said coating comprises less than about 1 wt. % of surfactants.

15. A facemask as defined in claim 1, wherein said coating further comprises antiblocking particles.

16. A facemask as defined in claim 1, wherein said coated substrate exhibits a transmission of normal incident light of greater than about 3% when compared to an uncoated substrate.

17. A facemask as defined in claim 1, wherein said coated substrate exhibits a transmission of normal incident light of greater than about 5% when compared to an uncoated substrate.

18. A facemask as defined in claim 1, wherein said coated substrate exhibits a transmission of normal incident light of greater than about 8% when compared to an uncoated substrate.

19. A facemask as defined in claim 1, wherein the haze of said substrate subtracted by the haze of an uncoated substrate is less than 0%.

20. A facemask as defined in claim 1, further comprising a filter body attached to said visor or shield.

21. A facemask comprising a transparent visor or shield, wherein a coating is present on at least one surface of said transparent visor or shield that consists essentially of one or more cellulosic ethers, wherein the one or more cellulosic ethers constitute at least about 90 wt. % of said coating, wherein said coating has a thickness of from about 50 to about 250 nanometers.

22. A facemask as defined in claim 21, wherein said one or more cellulosic ethers include an alkyl hydroxyalkyl cellulose ether.

23. A facemask as defined in claim 22, wherein said one or more cellulosic ethers include ethyl hydroxyethyl cellulose.

24. A facemask as defined in claim 21, wherein said coating comprises less than about 10 wt. % of surfactants.

25. A facemask as defined in claim 21, wherein said coating comprises less than about 1 wt. % of surfactants.

26. A method for forming a facemask that comprises a transparent substrate, said method comprising:
   applying an aqueous composition to at least one surface of the transparent substrate, said aqueous composition including a mixture of water and one or more water-soluble organic polymers selected from the group consisting of cellulosic ethers;
   drying said aqueous composition to form a coating on said transparent substrate, wherein said coating has a thickness of from about 50 to about 260 nanometers and consists essentially of one or more cellulosic ethers, wherein the one or more cellulosic ethers constitute at least about 90 wt. % of said coating, and the substrate forms a visor or shield of the facemask.

27. A method as defined in claim 26, wherein said one or more water-soluble organic polymers include a nonionic cellulosic ether.

28. A method as defined in claim 27, wherein said cellulosic ether includes an alkyl hydroxyalkyl cellulose ether.

29. A method as defined in claim 28, wherein said cellulosic ether includes ethyl hydroxyethyl cellulose.

30. A method as defined in claim 26, wherein water constitutes at least about 75 wt. % of said aqueous coating composition.

31. A method as defined in claim 26, wherein said one or more water-soluble organic polymers constitute from about 0.01 wt. % to about 5 wt. % of said aqueous coating composition.

32. A method as defined in claim 26, wherein said one or more water-soluble organic polymers constitute from about 0.2 wt. % to about 0.75 wt. % of said aqueous coating composition.

33. A method as defined in claim 26, further comprising attaching said visor or shield to a filter body.

34. A method as defined in claim 26, wherein said coating comprises less than about 10 wt. % of surfactants.

35. A method as defined in claim 26, wherein said coating comprises less than about 1 wt. % of surfactants.

* * * * *